United States Patent
Dubois et al.

(10) Patent No.: US 8,252,960 B2
(45) Date of Patent: Aug. 28, 2012

(54) PROCESS FOR MANUFACTURING ACROLEIN OR ACRYLIC ACID FROM GLYCERIN

(75) Inventors: Jean-Luc Dubois, Millery (FR); Yasuhiro Magatani, Yamagushi (JP); Kimito Okumura, Yamagushi (JP)

(73) Assignee: Arkema France, Colombes (FR)

( * ) Notice: Subject to any disclaimer, the term of this patent is extended or adjusted under 35 U.S.C. 154(b) by 188 days.

(21) Appl. No.: 12/988,355

(22) PCT Filed: Apr. 14, 2009

(86) PCT No.: PCT/JP2009/057818
§ 371 (c)(1),
(2), (4) Date: Nov. 11, 2010

(87) PCT Pub. No.: WO2009/128555
PCT Pub. Date: Oct. 22, 2009

(65) Prior Publication Data
US 2011/0160491 A1   Jun. 30, 2011

(30) Foreign Application Priority Data

Apr. 16, 2008 (WO) ................. PCT/IB2008/000919

(51) Int. Cl.
C07C 45/32    (2006.01)
(52) U.S. Cl. ........................................ 568/485; 568/486
(58) Field of Classification Search ............... 568/485, 568/486
See application file for complete search history.

(56) References Cited

U.S. PATENT DOCUMENTS

| 2,558,520 A | 6/1951 | Hoyt et al. |
| 4,366,088 A | 12/1982 | Daniel |
| 5,387,720 A | 2/1995 | Neher et al. |
| 7,396,962 B1 | 7/2008 | Dubois et al. |
| 7,655,818 B2 | 2/2010 | Dubois et al. |
| 2005/0020851 A1 | 1/2005 | Olbert et al. |

FOREIGN PATENT DOCUMENTS

| EP | 0995491 | 4/2000 |
| EP | 1147807 | 10/2001 |
| FR | 695931 | 12/1930 |
| FR | 2657792 | 8/1991 |
| WO | WO 2007/058221 | 5/2007 |

OTHER PUBLICATIONS

Tsukuda et al., "Production of Acrolein from Glycerol over Silica-Supported Heteropoly Acids", Catalysis Communications 8 (2007), p. 1349-1353.
Song-Hai Chai et al., "Sustainable Production of Acrolein: Gas-Phase Dehydration of Glycerol over 12-Tungstophosphoric Acid Supported on ZrO2 and SiO2", Green Chem., Oct. 2008, p. 1087-1093.
Song-Hai Chai et al., "Sustainable Production of Acrolein: Preparation and Characterization of Zirconia-Supported 12-Tungstophosphoric Acid Catalyst for Gas-Phase Dehydration of Glycerol", Applied Catalysis A General 353 (2009), p. 213-222.
Alhanash et al., "Hydrogenolysis of Glycerol to Propanediol Over Ru: Polyoxometalate Bifunctional Catalyst", Springer Science & Business Media LLC 2007, p. 307-311.

*Primary Examiner* — Sikarl Witherspoon
(74) *Attorney, Agent, or Firm* — Lynn B. Morreale

(57) ABSTRACT

The subject of the present invention is a process for preparing acrolein by dehydration of glycerin, characterized in that the dehydration is carried out in the presence of a catalyst comprising mainly a compound in which protons in a heteropolyacid are exchanged at least partially with at least one cation selected from elements belonging to Group 1 to Group 16 of the Periodic Table of Elements. The process according to the invention permits to obtain acrolein at higher yield.

11 Claims, No Drawings

PROCESS FOR MANUFACTURING ACROLEIN OR ACRYLIC ACID FROM GLYCERIN

BACKGROUND OF THE INVENTION

1. Field of the Invention

The present invention relates to a process for producing acrolein and/or acrylic acid from glycerol and, more particularly, to a process for preparing acrolein by dehydration of glycerol in the presence of a novel catalyst based on salt of heteropolyacid.

2. Description of Related Art

Fossil resources, such as oil cuts, for the chemical industry will be exhausted in a few decades. Resources of natural and renewable origin as alternative raw materials are consequently being studied more and more.

Acrolein, an important synthetic intermediate for the chemical industry is produced industrially by oxidation, in the gas phase, of propylene via the oxygen in the air in the presence of catalyst systems based on mixed oxides. Glycerol, derived from animal or vegetable oils in the production of bio diesel fuels or oleochemicals is one of the routes envisaged as a substitute for propylene, glycerol being able to produce acrolein when subjected to a catalytic dehydration reaction. Such a process makes it possible to thus respond to the concept of green chemistry within a more general context of environment protection.

A method for preparing acrylic acid in one step by the oxydehydration reaction of glycerol in the presence of molecular oxygen is disclosed in WO 06/114506. The principle of the method is based on the two consecutive dehydration and oxidation reactions:

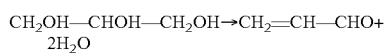

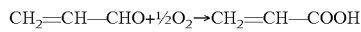

The presence of oxygen serves to carry out an oxidation reaction, following the glycerol dehydration reaction, leading to the formation of acrylic acid from the glycerol in a single step. This method can be implemented in the gas phase or the liquid phase, with concentrated or dilute aqueous solutions of glycerol. This method for producing acrylic acid directly from glycerol is particularly advantageous because it allows synthesis in a single reactor. However, it is necessary to introduce all the molecular oxygen from the dehydration stage. This has many drawbacks, in particular the reaction in the first dehydration step risks running out of control by combustion, and furthermore, when the source of molecular oxygen is air, the reactor must be much larger because of the presence of nitrogen in the air.

The use of an aqueous solution of glycerol in a two-step method has the drawback of producing, at the outlet of the first stage, a stream containing not only the acrolein produced and the by-products, but also a large quantity of water, originating partly from the glycerol solution, and partly from the water produced by the dehydration reaction. Use of aqueous solutions of glycerol, however, is preferable from economic reasons. This stream is sent to the second reactor, where the acrolein is oxidized to acrylic acid in the presence of a catalyst. The conventional catalysts for this oxidation reaction are generally solids containing at least one element selected from Mo, V, W, Re, Cr, Mn, Fe, Co, Ni, Cu, Zn, Sn, Te, Sb, Bi, Pt, Pd, Ru, Rh, present in metal form or oxide, nitrate, carbonate, sulphate or phosphate form. Certain elements, such as molybdenum, tellurium or rhenium, are volatile, particularly in the presence of water. This means that the second stage catalyst looses its efficiency and its mechanical strength rapidly in the presence of the stream of water, making the maintenance of the method difficult. Moreover, the acrylic acid, produced in a dilute aqueous solution, requires separation and concentration steps that are generally complicated and fairly costly.

Numerous catalyst systems have already been the subject of studies for the dehydration reaction of glycerol to acrolein.

A process is known from French Patent FR 695 931 for preparing acrolein from glycerol according to which acid salts having at least three acid functional groups or mixtures of these salts are used as catalysts. The preparation of these catalysts consists in impregnating, for example with iron phosphate, pumice that has been reduced to pea-sized fragments. According to the teaching of the patent, the yield obtained with this type of catalyst is greater than 80%.

In U.S. Pat. No. 2,558,520, the dehydration reaction is carried out in gas/liquid phase in the presence of diatomaceous earths impregnated with phosphoric acid salts, in suspension in an aromatic solvent. A degree of conversion of glycerol to acrolein of 72.3% is obtained under these conditions.

U.S. Pat. No. 5,387,720 discloses a process for producing acrolein by dehydration of glycerol in liquid phase or in gas phase at a temperature ranging up to 340° C., over acidic solid catalysts that are defined by their Hammett acidity. The catalysts must have a Hammett acidity below +2 and preferably below −3. These catalysts correspond, for example, to natural or synthetic siliceous materials, such as mordenite, montmorillonite and acidic zeolites; supports, such as oxides or siliceous materials, for example alumina ($Al_2O_3$), titanium oxide ($TiO_2$), covered by monobasic, dibasic or tribasic inorganic acids; oxides or mixed oxides such as gamma-alumina, $ZnO/Al_2O_3$ mixed oxide, or heteropolyacids. The use of these catalysts would make it possible to solve the problem of formation of secondary products generated with the iron phosphate type catalysts described in the aforementioned document FR 695,931.

According to International Application WO2006/087084, the strongly acidic solid catalysts whose Hammett acidity $H_0$ is between −9 and −18 have a strong catalytic activity for the dehydration reaction of glycerol to acrolein and are deactivated less quickly.

However, the catalysts recommended in the prior art for producing acrolein from glycerol generally lead to the formation of by-products such as hydroxypropanone, propanaldehyde, acetaldehyde, acetone, addition products of acrolein to glycerol, polycondensation products of glycerol, cyclic glycerol ethers, but also phenol and polyaromatic compounds which originate from the formation of coke on the catalyst and therefore from its deactivation. The presence of the by-products in acrolein, especially propanaldehyde, poses numerous problems for the separation of acrolein and requires separation and purification steps which lead to high costs for the recovery of the purified acrolein. Furthermore, when acrolein is used for producing acrylic acid, the propanaldehyde present may be oxidized to propionic acid that is difficult to separate from acrylic acid, especially by distillation. These impurities that are present greatly reduce the field of application of the acrolein produced by dehydration of glycerol.

The Applicant Company has therefore sought to improve the production of acrolein from glycerol, by using more selective catalysts that make it possible to obtain high yields of acrolein and that have an activity over long durations. In the field of catalysts, French Patent FR 2 657 792 discloses a catalyst of general formula $FeP_xMe_yO_z$, in which:

Me represents at least one of the following elements: Li, Na, K, Rb, Cs, Mg, Ca, Sr and Ba;
x has a value of 0.2 to 3.0;
y has a value of 0.1 to 2.0; and
z is the amount of oxygen bonded to the other elements and that corresponds to their oxidation state, this catalyst being combined with a support, characterized by the fact that said support is a fully impregnable macroporous support having a specific surface area less than or equal to 1 m²/g, a pore volume between 0.2 and 1 cm³/g and an average pore diameter greater than or equal to 1 micron, and that the active material is deposited on the surface of all the pores of said support, said catalyst being in the form of support grains impregnated with active material, which have a size between 0.5 and 10 mm.

French Patent FR 2 498 475 teaches to use a catalyst support to which a phosphate has been added by physical mixing with the catalyst that contains a phosphate, thus making it possible to partly solve the problem of extraction of phosphate during the use of the catalyst in the preparation of methacrylic acid from isobutyric acid and oxygen.

WO2007/058221 discloses a process for producing acrolein by dehydration reaction of glycerin in gas-phase in the presence of heteropolyacid used as a solid acid catalyst. The heteropolyacid is those of Group 6 element such as tungstosilicic acid, tungstophosphoric acid and phosphomolybdic acid. These heteropolyacids are supported on bi-elemental pore silica carrier and produce acrolein at a yield of 86%. This dehydration reaction of glycerin, however, is effected without oxidation gas but using nitrogen stream as carrier gas, so that deposition of carbon increase seriously and hence there is a problem of deterioration in time of stability, activity and selectivity of the catalysis.

Tsukida et al. "Production of acrolein from glycerol over silica-supported heteropoly acid" CATALYSIS COMMUNICATIONS, vol. 8, no. 9, 21 Jul. 2007, pp 1349-1353, and Chai et al., "Sustainable production of acrolein: gas phase dehydration of glycerol over 12-tungustophosphotic acid supported on $ZrO_2$ and $SiO_2$", GREEN CHEMISTRY, vol. 10, 2008, pp. 1087-1093, and Chai et al., "Sustainable production of acrolein: preparation and characterization of zirconia-supported 12-tungustophosphotic acid catalyst for gas phase dehydration of glycerol", APPLIED CATALYST A: GENERAL, vol. 353, 2009, pp. 213-222 disclose that silica or zirconia-supported heteropoly acid is effective as a catalyst for dehydration of glycerol.

In WO2006/087083, oxygen is introduced to prevent degradation of the catalyst in the gas-phase reaction of glycerin. In WO2006/087084, the catalyst possessing the acid strength of HO of −9 to −18 is used. A variety of solid acid catalysts such as phosphoric acid/zirconia, Nafion/silica, sulfuric acid/zirconia, tungsten/zirconia are used in Examples and the highest yield of acrolein of 74% was obtained when tungstated zirconia catalyst was used.

However, there is no catalyst usable in the industrial scale at higher performance.

Inventors of this application have made a variety of studies to solve the problems and found that acrolein and acrylic acid can be produced at high yield by using salt of heteropolyacid, in which protons in a heteropolyacid are exchanged at least partially with at least one cation selected from elements belonging to Group 1 to Group 16 of the Periodic Table of Elements, and completed this invention.

An object of this invention is to provide a process for producing acrolein and acrylic acid from glycerin that is a material not derived from petroleum, at a high yield.

SUMMARY OF THE INVENTION

This invention is characterized by following features (1) to (16) taken separately or in combination:
(1) Process for preparing acrolein by dehydration of glycerin, carried out in the presence of a catalyst comprising as a main component, at least one compound in which protons in a heteropolyacid are exchanged at least partially with at least one cation selected from elements belonging to Group 1 to Group 16 of the Periodic Table of Elements.
(2) The salt of heteropolyacid is represented by the general formula (1):

$$H_a A_b [X_1 Y_c Z_d O_e] \cdot n H_2 O \tag{1}$$

in which
H is hydrogen,
A is at least one cation selected from elements belonging to Group 1 to Group 16 of the Periodic Table of Elements except hydrogen,
X is P or Si,
Y is at least one element selected from the group comprising W, Mo, Ti, Zr, V, Nb, Ta, Cr, Mn, Fe, Co, Ni, Cu, Zn, Ga, In Tl, Sn and Pb,
Z is at least one element selected from the group comprising W, Mo, Ti, Zr, V, Nb, Ta, Cr, Mn, Fe, Co, Ni, Cu, Zn, Ga, In, Tl, Sn and Pb, and a, b, c and d being in following ranges:
$0 \leq a < 9$
$0 < b \leq 9$
$0 < c \leq 12$ and
$0 \leq d < 12$
e is a number determined by the oxidation numbers of the elements and n is any positive number (including 0) corresponding to a number of water molecules in the catalyst.
(3) The cation is at least one alkali metal cation.
(4) The alkali metal is cesium.
(5) The heteropolyacid is a heteropolyacid containing at least one element selected from the group comprising W, Mo and V.
(6) The process in which another compound of at least one element selected from elements belonging to Group 1 to Group 16 of the Periodic Table of Elements is used in addition to said salts of heteropolyacid.
(7) The catalyst is supported on a carrier.
(8) The catalyst is prepared by a method comprising by the steps of adding a solution of at least one metal selected from elements belonging to the Group 1 to Group 16 of the Periodic Table of Elements or onium to a solution of heteropolyacid, and of firing the resulting solid mixture.
(9) The calcination is carried out under an atmosphere of air, inert gas or a mixture of oxygen and inert gas.
(10) The calcination is effected at a temperature of 150 to 900° C. for 0.5 to 10 hours.
(11) The process is effected in the presence of molecular oxygen.
(12) The process is effected in the presence of a gas containing propylene.
(13) The process is performed in a reactor of the plate heat exchanger type or in a fixed bed reactor or in a fluidized bed type reactor or in a circulating fluidized bed or in a moving bed
(14) The resulting acrolein prepared by the process according to this invention can be further oxidized to produce acrylic acid.
(15) A process for preparing acrylic acid from glycerol comprises a first step of the dehydration reaction of glycerol to acrolein, in which an intermediate step of partial condensation of the water and heavy by-products issuing from the dehydration step is implemented.

(16) The process according to this invention can be used in a followed second step of ammoaxidation of acrolein to acrylonitrile, so that the resulting acrolein prepared by present invention is utilized effectively.

DESCRIPTION OF THE PREFERRED EMBODIMENTS

The dehydration catalyst according to this invention is used in dehydration of glycerin to produce acrolein and acrylic acid and comprises a compound in which protons of a heteropolyacid are exchanged at least partially with at least one cation selected from elements belonging to Group 1 to Group 16 of the Periodic Table of Elements.

The heteropolyacid is known and have a variety structures such as Keggin type, Dawson type and Anderson type and possess generally such high molecular weight as 700 to 8,500. Dimer complex of heteropolyacid are also included in the present invention.

Their acidic metal salt of elements belonging to Group 1 to Group 16 of the Periodic Table of Elements is used in the present invention. The salt may be salts of sodium, potassium, rubidium, cesium, magnesium, calcium, strontium, barium, scandium, yttrium, lanthanide, titanium, zirconium, hafnium, chromium, manganese, rhenium, iron, ruthenium, osmium, cobalt, nickel, palladium, platinum, copper, silver, gold, zinc, gallium, thallium, germanium, tin, lead, bismuth and tellurium. The onium salts of heteropolyacid acid may be amine salts, ammonium salts, phosphonium salts and sulfonium salts.

The dehydration catalyst for producing acrolein and acrylic acid from glycerin according to the present invention comprises preferably a salt or salts of heteropolyacid comprises at least one element selected from a group comprising W, Mo and V.

Ions of molybdenum and of tungsten form oxoacid in water and the resulting oxoacids polymerize to form the polyoxoacid of high molecular weight. The polymerization proceeds not only among same kind of oxoacids but also with other kinds of oxoacids. Heteropolyacid is a polyacid possessing polynuclear structure obtained by condensation of more than two kinds of such oxoacids. An atom that forms a center oxoacid is called as "hetero-atom",) while atoms forming oxoacids surrounding the center oxoacid and obtained by the polymerization is called as "poly-atoms". The heteroatom may be silicon, phosphorus, arsenic, sulfur, iron, cobalt, boron, aluminum, germanium, titanium, zirconium, cerium and chromium. Among them, phosphorus and silicon are preferable. The poly-atoms may be molybdenum, tungsten, vanadium, niobium and tantalum. Among them, molybdenum and tungsten are preferable. Salt forms of the heteropolyacids are used in this invention as glycerin dehydration catalyst. The heteropolyacid may be tungstophosphoric acid, tungstosilicic acid, phosphomolybdic acid and silicomolybdic acid. The heteropolyacid may be a mixed coordinate type comprising phosphorus or silicon as the heteroatom and molybdenum and tungsten as the poly-atoms, a mixed coordinate type of molybdenum and tungsten, a mixed coordinate type comprising tungsten and vanadium, or a mixed coordinate type comprising vanadium and tungsten.

In a preferred embodiment, the glycerin dehydration catalyst according to this invention consists mainly of a compound in which at least a part of protons in the heteropolyacid is exchanged with at least one cation of alkali metal. The alkali metal is preferably cesium. This type glycerin dehydration catalyst permits to produce acrolein and acrylic acid at high yield.

In a preferred embodiment, at least a part of protons in the heteropolyacid is exchanged with cesium and a part of remaining protons in the heteropolyacid is exchanged at least partially with at least one cation selected from elements belonging to Group 1 to Group 16 of the Periodic Table of Elements other than cesium. This type glycerin dehydration catalyst also is effective to produce acrolein and acrylic acid at high yield. Resistance to water is improved by exchanging part of protons contained in the heteropolyacid with cesium, so that the life of catalyst is improved in comparison to corresponding heteropolyacids that are inherently water-soluble.

The compound used in the present invention can be prepared by known technique. For example, an aqueous solution of heteropolyacid is prepared firstly. If necessary, water contained in the heteropolyacid in a form of adsorption water and/or crystalline water can be removed partially or perfectly under vacuum or by heat drying to prepare the aqueous solution of heteropolyacid. To the aqueous solution of heteropolyacid, an aqueous solution of halide, carbonate, acetate, nitrate, oxalate, phosphate or sulfate of metal or onium is added. From a resulting mixture, a solid component is separated by suitable treatment such as evaporation drying, filtering and vacuum drying. The resulting solid component is finally fired or calcinated to obtain the catalyst for glycerin dehydration reaction according to the present invention.

An amount of cation to be exchanged in the aqueous solution of mineral salt is determined in such a manner that an electric charge of cation to be added becomes equal to or less than an electric charge of the heteropolyanion. For example, when a cation with charges of 1+ is added to a heteropolyanion with charges of 3−, the cation is added in an amount equal to or less than 3 equivalent to the heteropolyanion. When a cation with charges of 3+ is added to a heteropolyanion with charges of 3−, the cation is added in an amount equal to or less than 1 equivalent to the heteropolyanion. When a plurality of cations is introduced, amounts of respective cations are determined in such a manner that the total electric charge of the cations becomes equal to or less than an electric charge of the heteropolyanion. If an amount of an aqueous solution of inorganic salt or a proportion of the cation(s) to be exchanged with protons become excessive, the activity of catalyst is spoiled, the yields of acrolein and acrylic acid are lowered, or the life of catalyst is shortened.

The catalyst according to the present invention used in the glycerin dehydration reaction may be in a form of either anhydride or hydrate. In fact, they can be used after pretreatment of firing and vacuum drying or without pretreatment.

The calcination can be carried out in air or under inert gas such as nitrogen, helium and argon or under an atmosphere of mixed gas of oxygen and inert gas, usually in a furnace such as muffle furnace, rotary kiln, fluidized bed furnace. Type of the furnace is not limited specially. The calcination can be effected even in a reaction tube that is used for the glycerin dehydration reaction. The firing temperature is usual 150 to 900° C., preferably 200 to 800° C. and more preferably 200 to 600° C. The calcination is continued usually for 0.5 to 10 hours.

In a variation, the glycerin dehydration catalyst according to this invention contains further at least one compound of element belonging to Group 1 to Group 16 of the Periodic Table of Element in addition to the salt of heteropolyacid. The compound of elements belonging to Group 1 to Group 16 of the Periodic Table of Element may be metal salts or onium salts. The metal salt may be salt of tellurium, platinum, palladium, iron, zirconium, copper, cerium, silver and aluminum. The onium salts may be amine salts, ammonium salts, phosphonium salts and sulfonium salts. The metal salt or the onium salt may be prepared from such materials as nitrates, carbonate, sulfates, acetates, oxides and halides of the metals or of onium but are not limited thereto. A proportion of the metal salt is 0.01 to 60% by weight, preferably 0.01 to 30% by weight in term of the metal salts or the onium salt with respect to the heteropolyacid salt.

The mostly preferred dehydration catalyst of glycerin is a compound having following composition represented by the general formula (1):

$$H_a A_b [X_1 Y_c Z_d O_e].n H_2 O \qquad (1)$$

in which

H is hydrogen,

A is at least one cation selected from elements belonging to Group 1 to Group 16 of the Periodic Table of Elements except hydrogen, X is P or Si, Y is at least one element selected from the group comprising W, Mo, Ti, Zr, Nb, Ta, Cr, Mn, Fe, Co, Ni, Cu, Zn, Ga, In, Tl, Sn and Pb, Z is at least one element selected from the group comprising W, Mo, Ti, Zr, Nb, Ta, Cr, Mn, Fe, Co, Ni, Cu, Zn, Ga, In, Tl, Sn and Pb, and a, b, c and d being in following ranges:

$0 \leq a < 9$ $0 < b \leq 9$ $0 < c \leq 12$ and $0 \leq d < 12$ e is a number determined by the oxidation numbers of the elements, and n is any positive number (including 0) corresponding to a number of water molecules in the catalyst.

In the glycerin dehydration catalyst according to this invention, the above compound can be supported on a carrier ("supported catalyst"). Examples of the carrier are silica, diatomaceous earth, alumina, silica alumina, silica magnesia, zirconia, titania, magnesia, zeolite, silicon carbide and carbon. The catalyst can be supported on a single carrier or a complex or mixture of at least two carriers. By supporting the active material in carrier, active components can be used effectively. An amount of the heteropolyacid salt is 5 to 200% by weight, preferably 5 to 150% by weight to the weight of the carrier.

In a variation, in place of supporting the compound in which protons in a heteropolyacid are exchanged with at least one cation selected from elements belonging to Group 1 to Group 16 of the Periodic Table of Elements, it is possible to effect such operation that heteropolyacid is applied firstly onto a carrier and then the exchange with cation is carried out.

The catalyst may have any shape and can be granule or powder. In case of gas phase reactions, however, it is preferable to mold the catalyst into a shape of sphere, pellets, cylinder, hollow cylinder, bar or the like, optionally with adding a molding aide. The catalyst can be shaped into the above-configurations together with carrier and optional auxiliary agents. The molded catalyst may have a particle size of for example 1 to 10 mm for a fixed bed and of less than 1 mm for a fluidized bed.

The dehydration reaction of glycerin according to this invention can be carried out in gas phase or in liquid phase and the gas phase is preferable. The gas phase reaction can be carried out in a variety of reactors such as fixed bed, fluidized bed, circulating fluidized bed and moving bed. Among them, the fixed bed and the fluidized bed are preferable. Regeneration of catalyst can be effected outside or inside the reactor.

The catalyst is regenerated in air or in oxygen-containing gas, or in hydrogen-containing gas. In case of liquid phase reaction, usual general type reactors for liquid reactions for solid catalysts can be used. Since a difference in boiling point between glycerin (290° C.) and acrolein (53° C.) and acrylic acid is big, the reaction is effected preferably at relatively lower temperatures so as to distil out acrolein continuously.

The reaction temperature for producing acrolein and acrylic acid by dehydration of glycerin in gas phase is effected preferably at a temperature of 450° C. to 200° C. If the temperature is lower than 200° C., the life of catalyst will be shortened due to polymerization and to carbonization of glycerin and of reaction products because the boiling point of glycerin is high. On the contrary, if the temperature exceeds 450° C., the selectivity of acrolein and acrylic acid will be lowered due to increment in parallel reactions and successive reactions. Therefore, more preferable reaction temperature is 250° C. to 350° C. The pressure is not limited specially but is preferably lower than 5 atm and more preferably lower than 3 atm. Under higher pressures, gasified glycerin will be re-liquefied and deposition of carbon will be promoted by higher pressure so that the life of catalyst will be shortened.

A feed rate of a reactant gas is preferably 500 to 10,000 h$^{-1}$ in term of the space velocity of GHSV (gas hourly space velocity). If the GHSV becomes lower than 500 h$^{-1}$, the selectivity will be lowered due to successive reactions. On the contrary, if the GHSV exceeds 10,000 h$^{-1}$, the conversion will be lowered.

The reaction temperature of the liquid phase reaction is preferably from 150° C. to 350° C. The selectivity will be spoiled under lower temperatures although the conversion is improved. The reaction pressure is not limited specially but the reaction can be carried, if necessary, under a pressurized condition of 3 atm to 70 atm.

The material of glycerin is easily available in a form of aqueous solution of glycerin. Concentration of the aqueous solution of glycerin is from 5% to 90% by weight and more preferably 10% to 50% by weight. Too higher concentration of glycerin will result in such problems as production of glycerin ethers or undesirable reaction between the resulting acrolein or acrylic acid and material glycerin. Still more, the energy that is necessary to gasify glycerin is increased.

The process according to the present invention is effected preferably in the presence of molecular oxygen. The molecular oxygen may be in a form of air or in a form of a mixture of gasses containing molecular oxygen. The presence of oxygen reduces the formation of aromatic compounds such as phenol and by-products such as propanaldehyde and acetone or from hydroxypropanone.

In the process of the invention, the reactant gas may also contain gas such as nitrogen, argon, carbon dioxide, sulfur dioxide.

The process according to the present invention can be effected in the presence of a gas containing propylene. In fact, the process according to the present invention is advantageously carried out in the presence of a reaction gas issued from an oxidation of propylene to acrolein. This reaction gas is generally a mixture of non-reacted propylene, propane initially presented in the propylene, inert gas, water vapour, oxygen, CO, CO$_2$, by products such as acrylic acid, acid or the like.

According to one particular embodiment of the invention, the process is performed in a reactor of the plate heat exchanger type. This reactor consists of plates forming between themselves circulation channels that can contain a catalyst. This technology has many advantages in terms of heat exchange, associated with high heat exchange capacity.

Thus, this type of reactor is particularly suitable for removing heat easily in the case of exothermic reactions, or for supplying heat in the start-up phases of reactions or in the case of endothermic reactions. More particularly, this reactor makes it possible either to heat or to cool the catalyst. The heat exchange is particularly efficient with the circulation of a heat-exchange fluid in the system. The plates may be assembled in modules, which gives greater flexibility, whether as regards the size of the reactor, its maintenance or the replacement of the catalyst. Systems that may be suitable for the process of the invention are, for example, the reactors described in documents EP 995 491 or EP 1 147 807, the content of which is incorporated by reference.

These reactors are particularly suitable for the catalytic conversion of reaction media, specifically gaseous reaction media, such as those used in the present invention. The plate heat exchanger used for the preparation of (meth)acrolein or (meth)acrylic acid via catalytic oxidation of C3 or C4 precursors, described in document US 2005/0020851, may also be suitable for the process according to this invention.

The resulting acrolein prepared by the process according to this invention can be further oxidized to produce acrylic acid.

In a preferred embodiment according to the present invention, a process for preparing acrylic acid from glycerol comprising a first step of the dehydration reaction of glycerol to acrolein, in which an intermediate step of partial condensation of the water and heavy by-products issuing from the dehydration step is implemented. In fact, the presence of water in the dehydration reactor serves to promote the gas phase glycerol dehydration reaction by limiting the deactivation of the dehydration catalyst. This process for synthesizing acrylic acid from glycerol can overcome the drawbacks of prior methods, while allowing the use of dilute aqueous solutions of glycerol that enhance the dehydration reaction while being economical. The solution provided by the invention constitutes an optimization between the quantity of water fed to the first stage dehydration reactor and the quantity of water introduced into the second stage oxidation reactor. The solution consists in at least partly condensing the water present in the stream issuing from the dehydration reaction of the aqueous glycerol solution, to prevent the second stage catalyst from being deactivated too rapidly, on the one hand, and to prevent the acrylic acid solution produced from being too dilute, on the other.

More precisely, the present invention relates to a method for preparing acrylic acid from an aqueous solution of glycerol, comprising a first step of dehydration of the glycerol to acrolein, carried out in the gas phase in the presence of a catalyst and under a pressure of between 1 and 5 bar, and a second step of oxidation of the acrolein to acrylic acid, in which an intermediate step, consisting in at least partly condensing the water and heavy by-products present in the stream issuing from the first dehydration step is implemented. The expression at least partly condensing means that 20% to 95%, preferably 40% to 90%, of the water present in the stream issuing from the first step is removed in the intermediate step before being sent to the second stage reactor.

The process according to this invention can be used advantageously in following second step of ammoxidation of acrolein to acrylonitrile, so that the resulting acrolein prepared by present invention is utilized effectively.

Now, the present invention will be explained in detail with referring illustrative examples but this invention should not be limited to those described in following examples. In the following Examples and Comparative Examples, % means mole %.

Example 1

Cesium salt of tungstophosphoric acid (CsPW) was prepared according to JP-A1-4-139149. Namely, 50 g of tungstophosphoric acid ($H_3[PW_{12}O_{40}]nH_2O$, n=about 30, a product of Nippon Inorganic Colour & Chemical Co., Ltd) was dissolved in 20 ml of pure water to obtain an aqueous solution of tungstophosphoric acid. In a separate beaker, 7.19 g of cesium nitrate ($CsNO_3$, Kishida Chemical Co., Ltd) was dissolved in 60 ml of water to obtain an aqueous solution of cesium nitrate. The aqueous solution of cesium nitrate was added under stirring drop-wise by means of a dropping funnel to the aqueous solution of tungstophosphoric acid. White slurry was generated at every dropping.

The resulting slurry was treated in a rotary evaporator under vacuum at 60° C. to obtain white powder. This powder was then dried at 150° C. for 6 hours in an oven at ambient pressure. Then, the resulting powder was fired in air at 250° C. for 3 hours by using a muffle furnace to obtain a catalyst (CsPW) of cesium salt of tungstophosphoric acid having a composition (proportions in materials; hereinafter, composition has the same meaning): $H_{0.5}Cs_{2.5}PW_{12}O_{40}$.

The catalyst was evaluated in a fixed bed reactor operated under ambient pressure in a fixed bed. Namely, the resulting catalyst powder was compacted and then crushed. Crushed particles were passed through sieves to obtain particles having a particle size of 9 to 12 mesh. 10 cc of the catalyst granules or particles was packed in a SUS reaction tube (diameter of 10 mm).

An aqueous solution of glycerin (a concentration of 20% by weight) was fed to an evaporator at a flow rate of 21 g/hr by a pump so that glycerin was gasified at 300° C. The resulting gasified glycerin was passed through the fixed catalyst bed together with air. The fixed catalyst bed was heated at a temperature of 260° C. to 350° C. Feed gas had a following composition in mol %:glycerin:oxygen:nitrogen:water=4.2:2.2:8.1:85.5. GHSV was 2,445 $h^{-1}$.

Products were condensed in a condenser and quantitative-analyzed by a gas chromatograph (product of GL Science, GC-4000, DB-WAX column). Proportions of products were corrected in factors from the results of the gas chromatograph to determine absolute amounts of products to calculate the conversion (%) of material (the conversion of glycerin), the selectivity of target substance (the selectivity of acrolein) and the yield of target substance (the yield of acrolein) from an amount of glycerin fed, an amount of glycerin remained and amounts of the products by following equations:

The conversion (%) of material=100*(a mole number of material reacted/a mole number of material supplied)

The selectivity (%) of objective substance=100*(a mole number of target substance obtained/a mole number of material reacted)

The yield (%) objective substance=100*(a mole number of target substance obtained/a mole number of material fed)

Result is shown in Table 1.

Example 2

Procedure of Example 1 was repeated except that 5.44 g of rubidium nitrate ($RbNO_3$) (Mitsuwa Chemicals Co., Ltd) was used instead of the cesium nitrate ($CsNO_3$) to prepare a catalyst of rubidium salt of tungstophosphoric acid (RbPW) having a composition: $H_{0.5}Rb_{2.5}PW_{12}O_{40}$.

Reaction and evaluation were effected under the same condition as Example 1.

Example 3

Procedure of Example 1 was repeated except that 3.22 g of calcium chloride, dihydrate ($CaCl_2 2H_2O$) (Wako Pure Chemical Industries, Ltd) was used instead of the cesium nitrate ($CsNO_3$) to prepare a catalyst of calcium salt of tungstophosphoric acid (CaPW) having a composition: $Ca_{1.5}PW_{12}O_{40}$.

Reaction and evaluation were effected under the same condition as Example 1.

Example 4

Procedure of Example 1 was repeated except that 5.96 g of ferric nitrate (III) nonahydrate ($Fe(NO_3)_3 9H_2O$) (Nihon Kagaku Sangyo Co., Ltd) was used instead of cesium nitrate ($CsNO_3$) to prepare iron salt of tungstophosphoric acid a catalyst (FePW) of calcium salt of tungstophosphoric acid having a composition: $FePW_{12}O_{40}$.

Reaction and evaluation were effected under the same condition as Example 1.

Example 5

Procedure of Example 1 was repeated except that 3.57 g of zirconium oxychloride octahydrates ($ZrOCl_2 8H_2O$) (Wako Pure Chemical Industries, Ltd) was used instead of the cesium nitrate ($CsNO_3$) to prepare zirconium salt of tungstophosphoric acid (ZrPW) having a composition: $Zr_{0.75}PW_{12}O_{40}$.

Reaction and evaluation were effected under the same condition as Example 1.

Example 6

Procedure of Example 1 was repeated except that 6.34 g of lanthanum nitrate ($La(NO_3)_3 6H_2O$) (Wako Pure Chemical Industries, Ltd) was used instead of the cesium nitrate ($CsNO_3$) to prepare lanthanum salt of tungstophosphoric acid (LaPW) having a composition: $LaPW_{12}O_{40}$.

Reaction and evaluation were effected under the same condition as Example 1.

Example 7

Procedure of Example 1 was repeated except that 3.53 g of hafnium chloride ($HfCl_4$) (Wako Pure Chemical Industries, Ltd) was used instead of the cesium nitrate ($CsNO_3$) to prepare hafnium salt of tungstophosphoric acid (HfPW) having a composition: $Hf_{0.75}PW_{12}O_{40}$.

Reaction and evaluation were effected under the same condition as Example 1.

Example 8

Bismuth salt of tungstophosphoric acid (BiPW) was prepared according to JP-A1-4-139149 and JP-A1-2006-110539. Namely, 50 g of tungstophosphoric acid ($H_3[PW_{12}O_{40}]nH_2O$, n=about 30, product of Nippon Inorganic Colour & Chemical Co., Ltd) was dissolved in 20 ml of pure water to obtain an aqueous solution of tungstophosphoric acid. In a separate beaker, 28.3 ml of 60% aqueous solution of nitric acid and 117.6 ml of water were added to 7.09 g of bismuth nitrate ($Bi(NO_3)_3$, Kishida Chemical Co., Ltd). The resulting aqueous solution of bismuth nitrate was added under stirring drop-wise by means of a dropping funnel to the aqueous solution of tungstophosphoric acid. Yellow white slurry was generated at every dropping.

The resulting slurry was dried by a rotary evaporator under vacuum at 60° C. to obtain white powder. This powder was then dried at 150° C. for 6 hours in an oven at ambient pressure. Then, the resulting powder was fired in air at 250° C. for 3 hours by using a muffle furnace to obtain a catalyst of bismuth salt of tungstophosphoric acid (BiPW) having a composition: $BiPW_{12}O_{40}$.

Example 9

In preparation of the cesium salt of heteropolyacid in Example 1, tungstosilicic acid was used instead of tungstophosphoric acid to prepare cesium salt of tungstosilicic acid (CsSiW).

Namely, 50 g of tungstosilicic acid (product of Nippon Inorganic Colour & Chemical Co., Ltd) was dissolved in 20 ml of pure water to obtain an aqueous solution of tungstosilicic acid. In a separate beaker, 7.43 g of cesium nitrate ($CsNO_3$, Kishida Chemical Co., Ltd) was dissolved in 60 ml of water to obtain an aqueous solution of cesium nitrate. The aqueous solution of cesium nitrate was added under stirring drop-wise by means of a dropping funnel to the aqueous solution of tungstosilicic acid. White slurry was generated at every dropping.

The resulting slurry was treated in a rotary evaporator under vacuum at 60° C. to obtain white powder. This powder was then dried at 150° C. for 6 hours in an oven at ambient pressure. Then, the resulting powder was fired in air at 250° C. for 3 hours by using a Muffle furnace to obtain cesium salt of tungstosilicic acid (CsSiW) having a composition: $H_{1.5}Cs_{2.5}SiW_{12}O_{40}$.

Reaction and evaluation were effected under the same condition as Example 1.

Comparative Examples 1 to 3

To compare with the salts of heteropolyacid, heteropolyacid alone was used and evaluated.

In Comparative Examples 1 to 3, as heteropolyacid, tungstophosphoric acid ($H_3[PW_{12}O_{40}]nH_2O$, n=about 30), tungstosilicic acid ($H_3[SiW_{12}O_{40}]nH_2O$, n=about 24) and phosphomolybdic acid ($H_3[PMo_{12}O_{40}]nH_2O$, n=about 30, products of Nippon Inorganic Colour & Chemical Co., Ltd) were used and fired at 250° C. in air for 3 hours in muffle furnace.

Reaction and evaluation were effected under the same condition as Example 1.

TABLE 1

| | Catalyst | Reaction temperature (° C.) | Glycerin conversion (%) | Acrolein yield (%) |
|---|---|---|---|---|
| Example 1 | CsPW | 260 | 100 | 92.9 |
| 2 | RbPW | 280 | 100 | 91.2 |
| 3 | CaPW | 350 | 78.6 | 49.8 |
| 4 | FePW | 300 | 99.0 | 70.9 |
| 5 | ZrPW | 350 | 82.5 | 60.6 |
| 6 | LaPW | 300 | 95.0 | 65.6 |
| 7 | HfPW | 350 | 84.6 | 62.1 |
| 8 | BiPW | 320 | 85.7 | 60.9 |
| 9 | CsSiW | 280 | 100 | 93.1 |
| Comparative Example 1 | PW | 320 | 74.0 | 54.8 |

TABLE 1-continued

| Catalyst | | Reaction temperature (° C.) | Glycerin conversion (%) | Acrolein yield (%) |
|---|---|---|---|---|
| 2 | SiW | 350 | 73.4 | 50.2 |
| 3 | PMo | 260 | 91.3 | 16.3 |

Example 10

This example was made to show that acrolein can be produced without adding oxygen by the process according to the present invention.

In the example, a tubular reactor consisting of a tube 85 cm long and with an inside diameter of 6 mm was used to perform the glycerol dehydration reaction in the gas phase at atmospheric pressure. This reactor is placed in a heated chamber maintained at the reaction temperature, which is 30° C. The catalyst was ground and pelletized to obtain particles of 0.5 to 1.0 mm. 10 ml of catalyst are loaded into the reactor to form a catalytic bed 35 cm long. This bed was maintained at the reaction temperature for 5 to 10 minutes before introducing the reagents. The reactor was fed with an aqueous solution containing 20% by weight of glycerol at a mean feed flow rate of 12 ml/h. The aqueous glycerol solution was vaporized in the heated chamber, and then passes over the catalyst. The calculated contact time was about 2.9 sec. The duration of a catalyst test was about 7 hours, which corresponds to about 80 ml of aqueous glycerol solution passed over the catalyst. After reaction, the products are condensed in a trap refrigerated with crushed ice. Samples of the effluents were collected periodically. For each sample collection, the flow was interrupted and a gentle flow of nitrogen was passed through the reactor to purge it. The trap at the reactor outlet was then replaced, the nitrogen flow was stopped and the reactor was returned under a flow of reagent. The test was continued until appreciable deactivation of the catalyst was noted.

For each experiment, the total mass of products entering and leaving was measured, which allowed a mass balance to be determined. Similarly, the products formed were analysed by chromatography. Two types of analysis were performed:
- an analysis by chromatography on a filled column (FFAP column 2 m*⅛") on a Carlo Erba chromatograph equipped with a TCD detector. The quantitative analysis was performed with an external standard (2-butanone);
- an analysis by chromatography on a capillary column (FFAP column 50 m*0.25 mm) on an HP6890 chromatograph equipped with an FID detector with the same samples stored at −15° C.

The first method was particularly suitable for rapid analysis of the products, and especially the yield of acrolein. The second method was used to have a more precise analysis of all the reaction by-products. Moreover, analyses by GC-MS or by chromatography after silylation were performed to confirm these results.

The products thus quantified were the unreacted glycerol, the acrolein formed and the by-products such as hydroxypropanone, acetaldehyde, propanaldehyde, acetone and phenol.

In the example, the glycerol conversion, the acrolein selectivity and the yields of the various products were defined as follows:

glycerol conversion (%)=100*number of moles of glycerol remaining/number of moles of glycerol introduced;

acrolein yield (%)=number of moles of acrolein produced/number of moles of glycerol introduced;

acrolein selectivity (%)=100*number of moles of acrolein produced/number of moles of glycerol reacted.

The acetone or hydroxypropanone yield was calculated as for the acrolein yield:

acetaldehyde yield (%)=⅔*number of moles of acetaldehyde produced/number of moles of glycerol introduced.

phenol yield (%)=2*number of moles of phenol produced/number of moles of glycerol introduced.

All the results were expressed as molar percentages relative to the glycerol introduced.

The catalyst used was cesium salt of phosphotungstic acid $Cs_{2.5}H_{0.5}PW_{12}O_{40}$ available on market (a product of Nippon Inorganic Colour & Chemical Co., Ltd). 10 ml (25.34 g) of the catalyst was loaded into the reactor. The results are summarized in Table 2 below:

TABLE 2

| | | | | | |
|---|---|---|---|---|---|
| Cumulative glycerol introduced (g) | 8 | 16 | 24 | 31 | 41 |
| Glycerol conversion | 83 | 56 | 49 | 42 | 57 |
| Acrolein yield | 39.4 | 39.5 | 32.3 | 27.8 | 37.8 |
| Acrolein selectivity | 47 | 70 | 66 | 66 | 66 |
| Hydroxypropanone yield | 2.4 | 3.9 | 2.3 | 2.0 | 4.6 |
| Acetaldehyde yield | 0.3 | 0.1 | 0.1 | 0.1 | 0.3 |
| Propanaldehyde yield | 3.2 | 2.1 | 0.4 | 1.0 | 3.5 |
| Acetone yield | 0.0 | 0.0 | 0.0 | 0.0 | 0.0 |
| Phenol yield | 0.2 | 0.0 | 0.0 | 0.8 | 0.0 |
| Material balance (mass collected/mass introduced) | 98.8 | 99.4 | 98.8 | 99.3 | 99.0 |
| Quantified product balance (products assayed/glycerol introduced) | 62.0 | 89.4 | 86.3 | 89.2 | 88.8 |

The process according to this invention in which glycerin is catalytic dehydrated to prepare acrolein and acrylic acid is very advantageous for industrial uses, because acrolein and acrylic acid can be produced at higher yield and in higher efficiency. In fact, the resistance to water is remarkably improved and deactivation of catalyst can be suppressed effectively by using salt of heteropolyacid according to this invention. On the contrary, in case of the conventional catalyst of heteropolyacids, deterioration or deactivation of catalysts is serious in a glycerin dehydration reaction in a gas phase which is effected in the presence of excess amount of water, such a reaction as using an aqueous solution of glycerin at lower concentration as material, or in a liquid phase in which water or lower alcohol is used as a reaction medium. Still more, owing to the improvement in resistance to water, a problem of corrosion of reactors that was observed when acid catalyst was used can be also solved Example 11

Powder of cesium salt of tungstophosphoric acid $(Cs_{2.5}H_{0.5}PW_{12}O_{40})$ (a product of Nippon Inorganic Colour & Chemical Co., Ltd) was fired in air at 250° C. for 3 hours by using a muffle furnace to obtain a catalyst.

The catalyst was evaluated in a fixed bed reactor operated under ambient pressure in a fixed bed. Namely, the resulting catalyst powder was compacted and then crushed. Crushed particles were passed through sieves to obtain particles having a particle size of 9 to 12 mesh. 10 cc of the catalyst granules or particles was packed in a SUS reaction tube (diameter of 20 mm).

An aqueous solution of glycerin (a concentration of 30% by weight) was fed to an evaporator at a flow rate of 21 g/hr by a pump so that glycerin was gasified at 300° C. The resulting gasified glycerin was passed through the fixed catalyst bed together with air. The fixed catalyst bed was heated at a temperature of 260° C. to 350° C. Feed gas had a following composition in mol %:glycerin:oxygen:nitrogen:water=6.3:4.0:14.9:74.8. GHSV was 2,445 $h^{-1}$.

Products were analyzed and the conversion (%) of material (the conversion of glycerin), the conversion of material (glycerin), the selectivity of target substances (the selectivity of acrolein and the selectivity of acrylic acid) and the yield of target substances (the yield of acrolein and the yield of acrylic acid) were calculated by the same method as Example 1. Result is shown in Table 3.

Example 12

50 g of cesium salt of tungstophosphoric acid ($Cs_{2.5}H_{0.5}PW_{12}O_{40}$) (a product of Nippon Inorganic Colour & Chemical Co., Ltd) was added with 80 ml of pure water. In a separate beaker, 0.008 g of chloroplatinate hexahydrates ($H_2PtCl_6 6H_2O$) (Wako Pure Chemical Industries, Ltd) was dissolved in 0.5 ml of water to obtain a solution which was then added under stirring dropwise to a white solution of the cesium salt of tungstophosphoric acid by using a dropping funnel.

The resulting slurry was treated in a rotary evaporator under vacuum at 60° C. to obtain white powder. This powder was then dried at 150° C. for 6 hours in an oven at ambient pressure. Then, the resulting powder was fired in air at 250° C. for 3 hours by using a muffle furnace to obtain a catalyst (Pt—CsPW) of platinum-added cesium salt of tungstophosphoric acid having a following composition: $Pr_{0.001}H_{0.5}Cs_{2.5}PW_{12}O_{40}$.

Reaction and evaluation were effected under the same condition as Example 11. Result is shown in Table 3.

Example 13

Procedure of Example 12 was repeated except that 0.492 g of iron nitrate nonahydrate ($Fe(NO_3)_3 9H_2O$) (NIHON KAGAKU SANGYO CO., LTD.) was used instead of the chloroplatinate hexahydrates ($H_2PtCl_6 6H_2O$) to prepare a catalyst of iron-added salt of tungstophosphoric acid (Fe—CsPW) having a composition: $Fe_{0.08}H_{0.26}Cs_{2.5}PW_{12}O_{40}$.

Reaction and evaluation were effected under the same condition as Example 11. Result is shown in Table 3.

Example 14

Procedure of Example 12 was repeated except that 0.488 g of chromium nitrate nonahydrate ($Cr(NO_3)_3 9H_2O$) (Wako Pure Chemical Industries, Ltd) was used instead of the chloroplatinate hexahydrates ($H_2PtCl_6 6H_2O$) to prepare a catalyst of iron-added salt of tungstophosphoric acid (Cr—CsPW) having a composition: $Cr_{0.08}H_{0.26}Cs_{2.5}PW_{12}O_{40}$.

Reaction and evaluation were effected under the same condition as Example 11. Result is shown in Table 3.

Example 15

Procedure of Example 12 was repeated except that 0.095 g of ammonium nitrate ($NH_4NO_3$) (Wako Pure Chemical Industries, Ltd) was used instead of the chloroplatinate hexahydrates ($H_2PtCl_6 6H_2O$) to prepare a catalyst of ammonium-added salt of tungstophosphoric acid ($NH_4$—CsPW) having a composition: $NH_{4\,0.08}H_{0.42}Cs_{2.5}PW_{12}O_{40}$.

Reaction and evaluation were effected under the same condition as Example 11. Result is shown in Table 3.

Example 16

Procedure of Example 12 was repeated except that 0.182 g of rubidium nitrate ($RbNO_3$) (Mitsuwa Chemical Co, Ltd) was used instead of the chloroplatinate hexahydrates ($H_2PtCl_6 6H_2O$) to prepare a catalyst of rubidium-added salt of tungstophosphoric acid (Rb—CsPW) having a composition: $Rb_{0.08}H_{0.42}Cs_{2.5}PW_{12}O_{40}$.

Reaction and evaluation were effected under the same condition as Example 11. Result is shown in Table 3.

Example 17

Procedure of Example 12 was repeated except that 1.751 g of telluric (VI) acid ($H_6TeO3$) (Shinko Chemical Co., Ltd.) was used instead of the chloroplatinate hexahydrates ($H_2PtCl_6 6H_2O$) to prepare a catalyst of tellurium-added salt of tungstophosphoric acid (Te—CsPW) having a composition: $Te_{0.5}H_{0.5}Cs_{2.5}PW_{12}O_{40}$.

Reaction and evaluation were effected under the same condition as Example 11. Result is shown in Table 3.

Example 18

Procedure of Example 12 was repeated except that 0.125 g of potassium nitrate ($KNO_3$) (Sigma Aldrich) was used instead of the chloroplatinate hexahydrates ($H_2PtCl_6 6H_2O$) to prepare a catalyst of potassium-added salt of tungstophosphoric acid (K—CsPW) having a composition: $K_{0.08}H_{0.42}Cs_{2.5}PW_{12}O_{40}$.

Reaction and evaluation were effected under the same condition as Example 11. Result is shown in Table 3.

Example 19

Procedure of Example 12 was repeated except that 0.327 g of ammonium perrhenate ($NH_4ReO_4$) (Mitsuwa Chemical Co, Ltd) was used instead of the chloroplatinate hexahydrates ($H_2PtCl_6 6H_2O$) to prepare a catalyst of rhenium-added salt of tungstophosphoric acid (Re—CsPW) having a composition: $Re_{0.08}H_{0.5}Cs_{2.5}PW_{12}O_{40}$.

Reaction and evaluation were effected under the same condition as Example 11. Result is shown in Table 3.

TABLE 3

| | Catalyst | Reaction temperature (° C.) | Glycerin conversion (%) | Acrolein yield (%) | Acrylic acid yield (%) |
|---|---|---|---|---|---|
| Example 11 | CsPW | 280 | 99.4 | 84.2 | 1.0 |
| 12 | Pt—CsPW | 260 | 100 | 74.0 | 4.6 |
| 13 | Fe—CsPW | 300 | 100 | 65.8 | 11.7 |
| 14 | Cr—CsPW | 300 | 100 | 61.4 | 15.2 |
| 15 | $NH_4$—CsPW | 280 | 99.8 | 82.9 | 1.1 |
| 16 | Rb—CsPW | 280 | 99.9 | 83.2 | 1.0 |
| 17 | Te—CsPW | 280 | 100 | 47.7 | 23.4 |
| 18 | K—CsPW | 280 | 99.9 | 87.1 | 1.1 |
| 19 | Re—CsPW | 280 | 100 | 86.2 | 1.1 |

Then, experiments were carried out by supporting the cesium tungstophosphate on niobia (niobium oxide). A degree of support was 30% by weight. The degree of support is calculated by following equation:

The degree of support (wt %)=100*(weight of cesium tungstophosphate)/(weight of cesium tungstophosphate+weight of support)

Example 20

15 g of cesium salt of tungstophosphoric acid ($Cs_{2.5}H_{0.5}PW_{12}O_{40}$) (a product of Nippon Inorganic Colour & Chemical Co., Ltd) was added with 250 ml of pure water and stirred. Into the resulting white solution of the cesium tungstophosphate, 35 g of support of niobia (Mitsui Mining & Smelting Co., Ltd.) and stirred for 2 hours in ambient temperature. The resulting slurry was dried in a rotary evaporator under vacuum at 60° C. to obtain white powder. This powder was then dried at 150° C. for 6 hours in an oven at ambient pressure. Then, the resulting powder was fired in air at 250° C. for 3 hours by using a muffle furnace.

Reaction and evaluation were effected under the same condition as Example 11. Result is shown in Table 4.

TABLE 4

| | carrier | Reaction temperature (° C.) | Glycerin conversion (%) | Acrolein yield (%) | Acrylic acid yield (%) |
|---|---|---|---|---|---|
| Example 20 | $Nb_2O_5$ | 300 | 99.7 | 84.4 | 0.6 |

From the comparison between Examples and Comparative Examples, followings are observed:
(1) In the production of acrolein by dehydration reaction of glycerin, the yield of acrolein can be increased remarkably such as higher than 90%, by using the catalyst according to the present invention, in particular, catalyst compounds in which proton in heteropoly acid such as PW and SiW is replaced at least partially by alkali metal, such as Cs or Rb.
(2) When heteropolyacid alone (which is outside the present invention) was used, the yield of acrolein is such poor as lower than 55% even in the highest yield of acrolein for PW (tungstophosphoric acid).
(3) The conversion of glycerin and the yield of acrolein are further increased by adding at least one element belonging to Group 1 to Group 16 of the Periodic Table of Elements, in particular, salts of K, Re to the cation exchanged compound.
(4) The conversion of glycerin and the yield of acrylic acid are further increased by adding at least one element belonging to Group 1 to Group 16 of the Periodic Table of Elements, in particular, salts of Pt, Fe, Cr and Te.
(5) Supported catalyst in which the cation exchanged compound is supported on carrier such as niobia show similar conversion of glycerin and similar yield of acrolein even if the cation exchanged compound is subjected to several times severer conditions.

The invention claimed is:
1. Process for preparing acrolein by dehydration of glycerin, characterized in that said dehydration is carried out in the presence of a catalyst comprising at least one compound in which protons in a heteropolyacid are exchanged at least partially with at least one cation selected from elements belonging to Group 1 to Group 16 of the Periodic Table of Elements.
2. The process of claim 1, wherein said compound is represented by the general formula (1):

$$H_aA_b[X_1YcZ_dO_e]\cdot nH_2O \qquad (1)$$

in which
H is hydrogen,
A is at least one cation selected from elements belonging to Group 1 to Group 16 of the Periodic Table of Elements except hydrogen,
X is P or Si,
Y is at least one element selected from the group consisting of W, Mo, Ti, Zr, V, Nb, Ta, Cr, Mn, Fe, Co, Ni, Cu, Zn, Ga, In, Tl, Sn and Pb,
Z is at least one element selected from the group consisting of W, Mo, Ti, Zr, V, Nb, Ta, Cr, Mn, Fe, Co, Ni, Cu, Zn, Ga, In, Tl, Sn and Pb,
a, b, c and d being in following ranges:
$0 \leq a < 9$,
$0 < b \leq 9$,
$0 < c \leq 12$,
$0 \leq d < 12$,
e is a number determined by the oxidation number of the elements and n is any positive number including 0.
3. The process of claim 1, wherein said at least one cation is at least one alkali metal cation.
4. The process of claim 3, wherein said alkali metal is cesium.
5. The process of claim 1, wherein said compound contains at least one element selected from the group consisting of W, Mo and V.
6. The process of claim 1, wherein said compound further contains a second element selected from elements belonging to Group 1 to Group 16 of the Periodic Table of Elements.
7. The process of claim 1, wherein said compound is supported on a carrier.
8. The process of claim 7, wherein said carrier is selected from the group consisting of titania, silica, zirconia, niobia, magnesia, ceria, alumina and silico-alumina.
9. The process of claim 1, wherein said catalyst is prepared by the steps of adding a solution of at least one metal selected from elements belonging to the Group 1 to Group 16 of the Periodic Table of Elements or onium to a solution of heteropolyacid, and of firing the resulting solid mixture.
10. The process of claim 9, wherein the firing is carried out under an atmosphere of air, inert gas or a mixture of oxygen and inert gas.
11. The process of claim 9, wherein the firing is effected at a temperature of 150 to 900° C. for 0.5 to 10 hours.

* * * * *